(12) United States Patent
Wong et al.

(10) Patent No.: US 12,146,823 B2
(45) Date of Patent: *Nov. 19, 2024

(54) SYSTEMS AND METHODS FOR CELL DISSOCIATION

(71) Applicant: Thrive Bioscience, Inc., Beverly, MA (US)

(72) Inventors: Kam Lin Wong, Bedford, MA (US); Melanie Scully, Beverly, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/186,827

(22) Filed: Mar. 20, 2023

(65) Prior Publication Data

US 2023/0304918 A1    Sep. 28, 2023

Related U.S. Application Data

(63) Continuation of application No. 16/614,538, filed as application No. PCT/US2018/033413 on May 18, 2018, now Pat. No. 11,662,296.

(Continued)

(51) Int. Cl.

| *G01N 15/1433* | (2024.01) |
| *C12M 1/34* | (2006.01) |
| *C12M 1/36* | (2006.01) |
| *G01N 15/1434* | (2024.01) |
| *G02B 21/32* | (2006.01) |
| *G16B 50/30* | (2019.01) |
| *G01N 15/14* | (2006.01) |
| *G01N 21/64* | (2006.01) |

(52) U.S. Cl.
CPC ......... *G01N 15/1433* (2024.01); *C12M 41/46* (2013.01); *C12M 41/48* (2013.01);
(Continued)

(58) Field of Classification Search
CPC .......... G01N 15/1463; G01N 15/1434; G01N 15/1475; G01N 21/6458;
(Continued)

(56) References Cited

U.S. PATENT DOCUMENTS 11,662,296 B2 *  5/2023  Wong ............... G16B 50/30
                                                       382/133
2003/0059103 A1   3/2003  Shiomi et al.
(Continued)

FOREIGN PATENT DOCUMENTS

CN    102087738 A    6/2011
EP       1661980 A1    5/2006
(Continued)

OTHER PUBLICATIONS

Extended European Search Report mailed Jul. 13, 2021, for Application No. EP 18803296.5.
(Continued)

*Primary Examiner* — Michael L Hobbs
(74) *Attorney, Agent, or Firm* — Wolf, Greenfield & Sacks, P.C.

(57) ABSTRACT

A system for dissociating cells from a cell culture vessel. The system comprises an imaging system configured to image a plurality of cells in a cell culture vessel being dissociated from at least one surface of the cell culture vessel by at least one cell dissociation agent; and at least one controller coupled to the imaging system and configured to: control the imaging system to capture a sequence of images of at least some cells in the plurality of cells during dissociation; and identify when to neutralize the at least one cell dissociation agent using the sequence of images.

21 Claims, 7 Drawing Sheets

Related U.S. Application Data

(60) Provisional application No. 62/508,955, filed on May 19, 2017.

(52) U.S. Cl.
CPC ......... *G01N 15/1434* (2013.01); *G02B 21/32* (2013.01); *G16B 50/30* (2019.02); *G01N 2015/1447* (2013.01); *G01N 2015/1452* (2013.01); *G01N 2015/1493* (2013.01); *G01N 2015/1497* (2013.01); *G01N 21/6458* (2013.01)

(58) Field of Classification Search
CPC ... G01N 2015/1447; G01N 2015/1452; G01N 2015/1493; G01N 2015/1497; G01N 2015/1006; G01N 2015/1495; G02B 21/32; G16B 50/30; C12M 33/00; C12M 41/36; C12M 41/48; C12M 41/46
See application file for complete search history.

(56) References Cited

U.S. PATENT DOCUMENTS

| | | | |
|---|---|---|---|
| 2004/0004614 A1* | 1/2004 | Bacus | G02B 21/367 345/419 |
| 2005/0051723 A1 | 3/2005 | Neagle et al. | |
| 2006/0115889 A1 | 6/2006 | Nakashima et al. | |
| 2009/0081769 A1 | 3/2009 | Kiyota et al. | |
| 2010/0291619 A1* | 11/2010 | Robinson | G01N 35/0099 435/288.7 |
| 2011/0102438 A1 | 5/2011 | Mathe et al. | |
| 2012/0258440 A1 | 10/2012 | Jung et al. | |

FOREIGN PATENT DOCUMENTS

| | | |
|---|---|---|
| JP | 2006-149268 A1 | 6/2006 |
| WO | WO 2007/136073 A1 | 10/2009 |
| WO | WO 2016/161163 A2 | 10/2016 |

OTHER PUBLICATIONS

International Search Report and Written Opinion mailed Sep. 7, 2018, for Application No. PCT/US2018/033413.

International Preliminary Report on Patentability mailed Nov. 28, 2019, for Application No. PCT/US2018/033413.

[No Author Listed], New Development of Communication Theory and Technology in 2008—13th National Youth Communication Conference of China Proceedings. Edited by Youth Working Committee of China Institute of Communications. National Defense Industry Press. Dec. 2008. pp. 1120-1123.

Artym et al., Imaging cells in three-dimensional collagen matrix. Curr Protoc Cell Biol. Sep. 2010;Chapter 10:Unit 10.18.1-20.

Bunnell et al., Adipose-derived stem cells: isolation, expansion and differentiation. Methods. Jun. 2008;45(2):115-20. doi: 10.1016/j.ymeth.2008.03.006. Epub May 29, 2008.

* cited by examiner

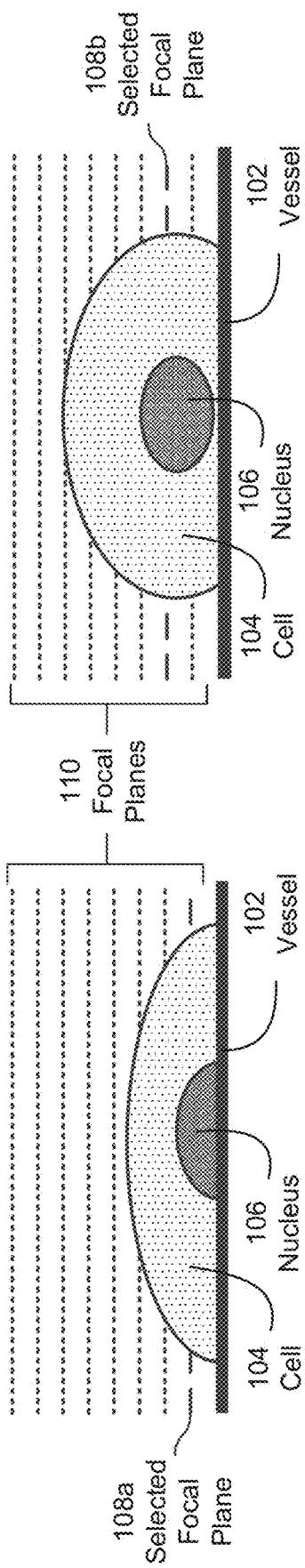
FIG. 1A
FIG. 1B
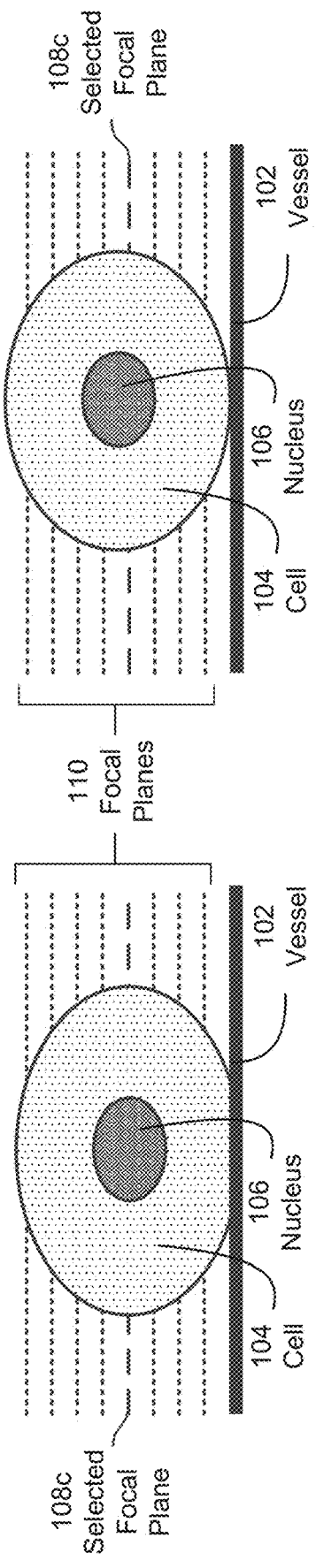
FIG. 1C
FIG. 1D

SYSTEMS AND METHODS FOR CELL DISSOCIATION

CROSS REFERENCE TO RELATED APPLICATIONS

This application is a continuation of U.S. patent application Ser. No. 16/614,538, filed Nov. 18, 2019, now U.S. Pat. No. 11,662,296, entitled "SYSTEMS AND METHODS FOR CELL DISSOCIATION," which is a national stage filing under 35 U.S.C. § 371 of International Application No. PCT/US2018/033413, filed May 18, 2018, entitled "SYSTEMS AND METHODS FOR CELL DISSOCIATION," which claims the benefit under 35 U.S.C. § 119 (e) to U.S. Provisional Application Ser. No. 62/508,955, entitled "SYSTEMS AND METHODS FOR CELL DISSOCIATION," filed on May 19, 2017, each of which is herein incorporated by reference in its entirety.

FIELD

Aspects of the technology described herein relate to techniques for cell dissociation using a cell dissociation agent. Some aspects relate to implementation of these techniques in cell culture incubators.

BACKGROUND

Cells are often cultivated in vessels such as a flask, a bottle, a bag, or a plate. In these vessels, the cells are typically provided a growth medium comprising nutrients for the cells. Cells typically adhere to one or more surfaces of the vessel as they grow. Once the cells become nearly (or fully) confluent, the cells in the vessel are passaged to allow the cells to continue growing. The cells may be passaged by detaching the cells from the vessel, either mechanically (e.g., by using gentle scraping or tapping) and/or enzymatically (e.g., using Trypsin or one or more other enzymes), and transferring the cells to one or more new vessels for further growth.

SUMMARY

Some embodiments are directed to a system, comprising: an imaging system configured to image a plurality of cells in a cell culture vessel being dissociated from at least one surface of the cell culture vessel by at least one cell dissociation agent; and at least one controller coupled to the imaging system. The at least one controller is coupled to memory storing instructions that when executed: control the imaging system to capture a sequence of images of at least some cells in the plurality of cells during dissociation; and use said sequence of images to identify when to neutralize the at least one cell dissociation agent.

Some embodiments are directed to a method, comprising: receiving a cell culture vessel storing a plurality of cells being dissociated from at least one surface of the cell culture vessel by at least one cell dissociation agent; capturing, by an imaging system, a sequence of images of at least some cells in the plurality of cells during dissociation; and identifying, using at least one controller coupled to the imaging system, when to neutralize the at least one cell dissociation agent using the sequence of images.

Some embodiments are directed to a cell culture incubator comprising: an incubator cabinet configured to receive a cell culture vessel storing a plurality of cells being dissociated from at least surface of the cell culture vessel by at least cell dissociation agent; an imaging system configured to image the plurality of cells; and at least one controller coupled to the imaging system. The at least one controller is coupled to memory containing instructions that when executed: control the imaging system to capture a sequence of images of at least some cells in the plurality of cells during dissociation; and use the sequence of images to identify when to neutralize the at least one cell dissociation agent.

Some embodiments are directed to a system, comprising: an imaging system configured to image a plurality of cells in a cell culture vessel being dissociated from at least one surface of the cell culture vessel by at least one cell dissociation agent; and at least one controller coupled to the imaging system. The at least one controller is coupled to memory storing instructions that when executed: control the imaging system to capture a sequence of images of at least some cells in the plurality of cells during dissociation; and use the sequence of images to identify when to mechanically separate the at least some cells from the at least one surface of the cell culture vessel.

Some embodiments are directed to a system comprising: an imaging system configured to image a plurality of cells in a cell culture vessel; and at least one controller coupled to the imaging system. The at least one controller is coupled to memory storing instructions that when executed: control the imaging system to capture a focused image of at least one cell in the plurality of cells; identify at least one morphological characteristic of the at least one cell using the focused image; identify at least one texture feature of the at least one cell using the focused image; and identify a cell type of the at least one cell using the identified at least one morphological characteristic of the at least one cell and the identified at least one texture feature of the at least one cell.

BRIEF DESCRIPTION OF DRAWINGS

Various aspects and embodiments will be described with reference to the following figures. It should be appreciated that the figures are not necessarily drawn to scale. Items appearing in multiple figures are indicated by the same or a similar reference number in all the figures in which they appear.

FIGS. 1A-1D are diagrams illustrating how shape of a cell changes shape during dissociation;

DETAILED DESCRIPTION

Figure 2A:
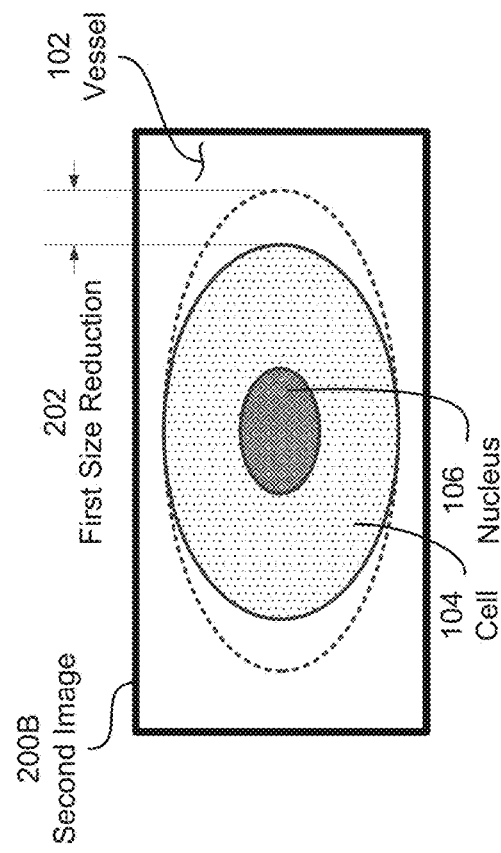
FIGS. 2A-2D are diagrams illustrating example images of a cell for each of the shapes shown in FIGS. 1A-1D, according to some embodiments of the technology described herein.

As discussed above, cells may be dissociated from a surface of a cell culture vessel by exposing the cells to a cell dissociation agent. The cell dissociation agent may comprise an enzyme such as Trypsin and/or an acid such as ethylenediaminetetraacetic acid (EDTA). However, the cells may become damaged or die if they are exposed to the cell dissociation agent for too long. Conventionally, cell culture technicians dissociate cells from a cell culture vessel by: (1) exposing the cells to a cell dissociation agent; (2) manually monitoring the cells to identify when the cells are sufficiently detached from the vessel (e.g., by periodically shaking or tapping the cell culture vessel and watching the cells react); and (3) neutralizing the cell dissociation agent (e.g., by adding a neutralizing agent and/or additional culture medium) to the cell culture vessel.

The inventor has recognized and appreciated that manually dissociating cells from a vessel is not only a time-consuming process that requires a cell culture technician's time, but also is subject to human error, as it requires the cell culture technician to make judgment calls as to when cells are or are not sufficiently detached from the surface(s) of the cell culture vessel. Accordingly, aspects of the technology described herein relate to image processing-based techniques for automatically determining when the cells are sufficiently detached from the cell culture vessel such that the cell dissociation agent may be neutralized and the cells may be transferred to one or more other vessels. These techniques improved upon conventional cell dissociation techniques by providing an objective and consistent basis for determining when cells have dissociated, which reduces human error and promotes cell viability.

In some embodiments, the image processing techniques, developed by the inventor, involve: (1) capturing a sequence of images (e.g., phase contrast images) of cells in a cell culture vessel; (2) extracting image features from at least some of the images in the sequence; (3) providing those images to a classifier (e.g., a neural network, a discriminant function, a Bayesian network, a Gaussian mixture model, a support vector machine, etc.); and (4) determining, based on output of the classifier, whether to neutralize the cell dissociation agent and/or mechanically remove the cells from the cell culture vessel. When it is determined, based on output of the classifier, that the cell dissociation agent is to be neutralized and/or the cells should be removed from the cell culture vessel, one or both of these steps may be taken (manually and/or automatically within a cell culture incubator). On the other hand, when it is determined, based on output of the classifier, that it is not yet time to neutralize the cell dissociation agent, automated monitoring of the cells may continue-additional images of the cells may be obtained and similarly analyzed to determine when to neutralize the cell dissociation agent and/or mechanically remove the cells from the cell culture vessel. Such automated imaging analysis may continue until it is determined that the cells have sufficiently detached from the cell culture vessel such that the cell dissociation agent may be neutralized and/or the cells may be removed from the cell culture vessel.

In some embodiments, the image features extracted from images in the sequence of images may reflect one or more morphological characteristics of the cells and/or how such characteristics change over time during dissociation. For example, the shape of a cell may change over time during dissociation, as the surface area over which the cells are in contact with the vessel decreases over time. Indeed, as cells dissociate from the cell culture vessel, the shape of the cells in the images progressively changes from being irregular (e.g., oval or oblong) to be more round. This is illustrated and further described below with reference to FIGS. 1A-1D. The rate at which cell shape changes from an irregular to a round shape also changes over time, and a reduction in that rate may signal that the cells have substantially detached from the cell culture vessel.

Accordingly, in some embodiments, at least some of the image features extracted from images in the sequence of images may reflect changes in cell shape and/or the rate of such changes. For example, in some embodiments, the image features may include foreground areas of one or more images (the foreground area of an image is the area of the portion of the image determined to include cells), background areas of one or more images (the background area of an image is the area of the portion of the image determined to not include cells), and histograms of one or more images. The inventor has appreciated that changes in such features may be indicative of changes of cell shape and the rate of such changes. Accordingly, these features and differences among these features when computed from different images, may be used to determine when to neutralize a cell dissociation agent and/or mechanically remove cells from the cell culture vessel, in some embodiments.

The inventor has also recognized and appreciated that as cells start to detach from the cell culture vessel, the depth at which the cells are imaged may need to be changed in order to accurately estimate the cell shapes and/or areas. Accordingly, in some embodiments, obtaining a sequence of images may including obtaining a sequence of image sets. Each image set may include multiple images taken at different focal lengths such that each image in the image is associated with a respective focal plane. Such an image set may be termed a "Z stack" as it may include two-dimensional (x-y) images at different focal lengths (different "z" coordinates) relative to the imager. A single "focused" image in each image set may be selected resulting in a sequence of focused images being selected from a respective sequence of image sets. In turn, the sequence of focused images may be used to derive image features to provide to a classifier for determining whether to neutralize a cell dissociation agent and/or mechanically remove cells from the cell culture vessel.

In some embodiments, a focused image may be selected from an image set by using one or more edge detection techniques. For example, in some embodiments, a focused image may be selected from an image set by detecting cell edges in each image (e.g., using at least one gradient operator, a Sobel edge detector, a Canny edge detector, etc.), determining edge strength (e.g., as a difference in image intensity along the edge), and using the edge strength to compute a focus score (e.g., as a normalized sum of squared edge strengths). The image associated with the smallest focus score may be selected as the focused image in the image set.

Figure 7:
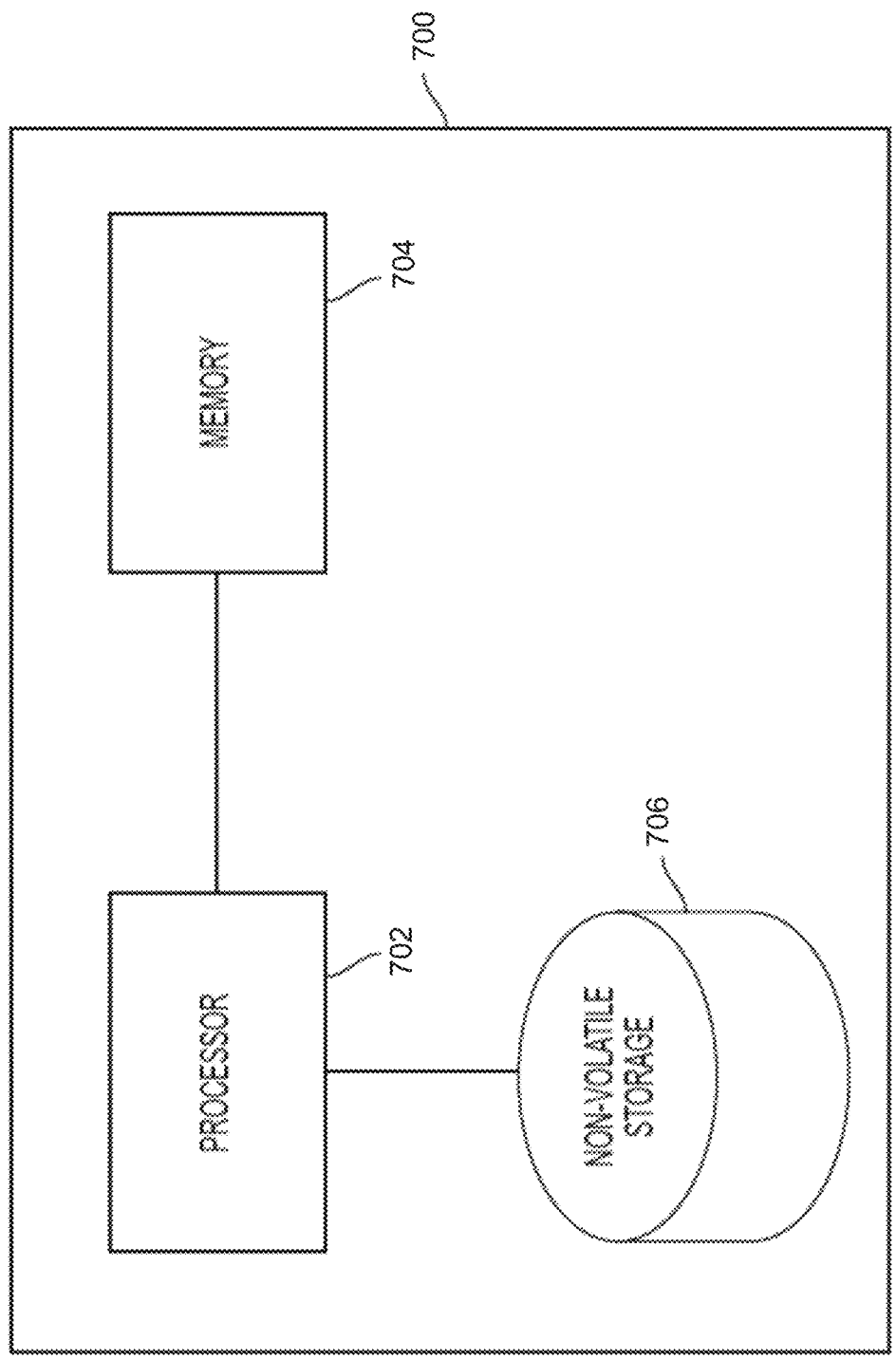
FIG. 7 is a block diagram of an illustrative controller, according to some embodiments of the technology described herein.

In some embodiments, the image-based techniques described herein may be performed by a cell culture incubator such as illustrative cell culture incubator described with reference to FIG. 7. The cell culture incubator may include: (1) an incubator cabinet configured to position a cell culture vessel storing a plurality of cells being dissociated from the cell culture vessel by at least one cell dissociation agent; (2) an imaging system configured to image cells in the cell culture vessel; and (3) at least one controller configured control the imaging system to capture a sequence of images of at least some cells in the plurality of cells during dissociation; and identify when to neutralize the at least one cell dissociation agent using the sequence of images.

As discussed above, some of the image features obtained from images reflect one or more morphological characteristics of cells (e.g., cell shape, cell size, nuclear size, and nuclear shape) in a cell culture vessel. In some embodiments, such image features may be used for purposes other than determining when to neutralize a cell dissociation agent. For example, the image features may be employed to identify the type or types of cells in the cell culture. In one implementation for illustration, the cell culture may contain stem cells that are capable of producing various daughter cells. In this implementation, image features may be extracted from an image of the cell culture, morphological characteristics of the cells may be identified using the image features, and the presence (or absence) of one or more types of stem cells and/or daughter cells may be identified using the identified morphological characteristics. Additional image features may also be employed in combination with the identified morphological characteristics to identify the type or types of cells in the cell culture such as light intensity features and/or texture features. Light intensity features may relate to, for example, characteristics of the intensity values of pixels that comprise an object (e.g., a cell). Texture features may relate to, for example, an appearance of a surface and/or a cross-section of an object (e.g., a cell).

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIGS. 1A-1D are diagrams illustrating how the shape of cell 104 changes over time during dissociation from a surface of vessel 102. As shown in FIGS. 1A-1D, the shape of the cell progressively changes during dissociation from irregular (in this example, most oblong in FIG. 1A) to round (in this example, most round in FIG. 1D).

Figure 3A:
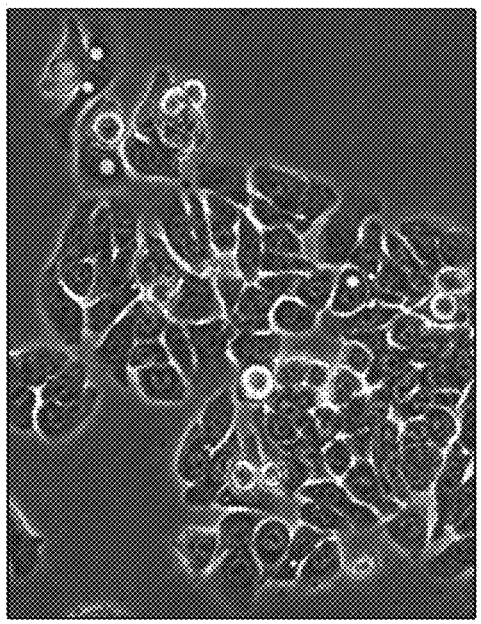
FIGS. 3A-3D are diagrams showing four different images of cells in a cell culture vessel during dissociation, according to some embodiments of the technology described herein.
Figure 3B:
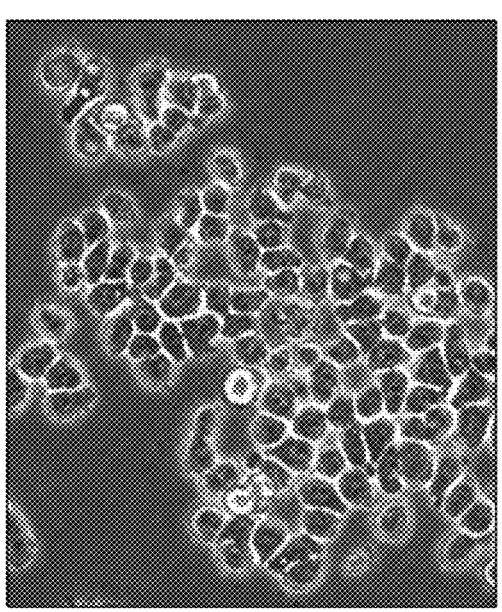
Figure 3C:
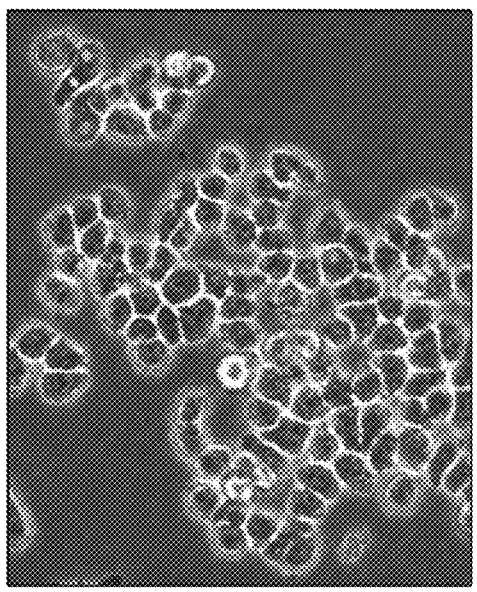
Figure 3D:
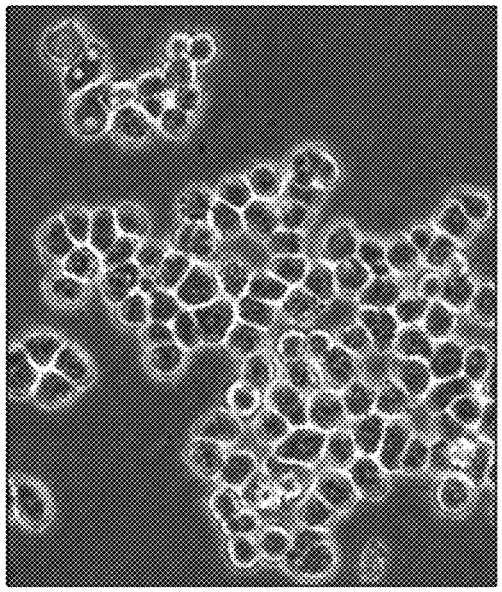

A similar change to cell shapes may be seen in FIGS. 3A-3D, which show images of cells undergoing dissociation over time. FIG. 3A shows a phase-contrast image of cells in a cell culture vessel immediately after a cell dissociation agent (Trypsin, in this illustrative example) has been added to the cell culture vessel. FIG. 3B shows a phase-contrast image of the cells approximately one minute after the dissociation agent has been added to the cell culture vessel. FIG. 3C shows a phase-contrast image of the cells approximately two minutes after the dissociation agent has been added to the cell culture vessel. FIG. 3D shows a phase-contrast image of the cells approximately four minutes after the dissociation agent has been added to the cell culture vessel. As can be seen from FIGS. 3A-3D, after exposure to the cell dissociation agent, the shape of the cells progressively changes from irregular (in this example, most oblong in FIG. 3A) to round (in this example, most round in FIG. 3D). These figures also show that the rate of change is not uniform, as the shape changes to a greater extent in the first two minutes of exposure to the cell dissociation agent (e.g., compare shapes of cells in FIG. 3A and FIG. 3C) than in the last two minutes of exposure (e.g., compare shapes of cells in FIG. 3C and FIG. 3D). As discussed above, since cell shape changes over time, in some embodiments, image features may be extracted from images obtained at different focal lengths at different times during the dissociation process in order to obtain accurate estimates of cell characteristics such as cell shape. For example, the cells in FIG. 3A and FIG. 3D may be imaged at different focal lengths in order to accurately determine cell shapes and/or other image features from the resultant images.

Accordingly, in some embodiments, to obtain an image from which to extract image features (which image features may be used subsequently for determining whether to neutralize the cell dissociation agent), an imaging device may capture multiple images of the cells at different focal lengths and select, from among the multiple images, a single "focused" image from which image features of interest may be determined. Techniques for selecting a single focused image from a set of images (e.g., a depth or "Z" stack of images) are described herein including the edge detection-based techniques described with reference to FIG. 5.

For example, as shown in FIGS. 1A-1D, the cell 104 may be imaged at four different time periods at focal lengths corresponding to focal planes 110 to obtain four different image sets. In this example, the cell 104 is imaged at different focal planes immediately after adding a cell dissociation agent, approximately one minute after adding the cell dissociation agent, approximately two minutes after the cell dissociation agent, and approximately three minutes after adding the cell dissociation agent. Each of the four image sets contains images for each of the focal planes 110. Within each of the four image sets, a single image may be selected from which to extract image features. In this example, the images obtained at focal lengths corresponding to focal planes 108a, 108b, 108c, and 108c may be selected, respectively, from the four image sets. Images corresponding to different focal planes are selected in the first three time periods as the shape of cell 104 changes over these time periods, becoming more round and with the nucleus 106 moving further away from the surface of cell culture vessel 102, as shown in FIGS. 1A-1C. On the other hand, images corresponding to the same focal plane 108c may be selected from the Z stacks obtained in the third and fourth time periods because the shape of cell 104 does not change sufficiently to warrant imaging at different focal lengths. In this example, cell 104 may appear focused at the same focal length during the third and fourth time periods.

Figure 2B:
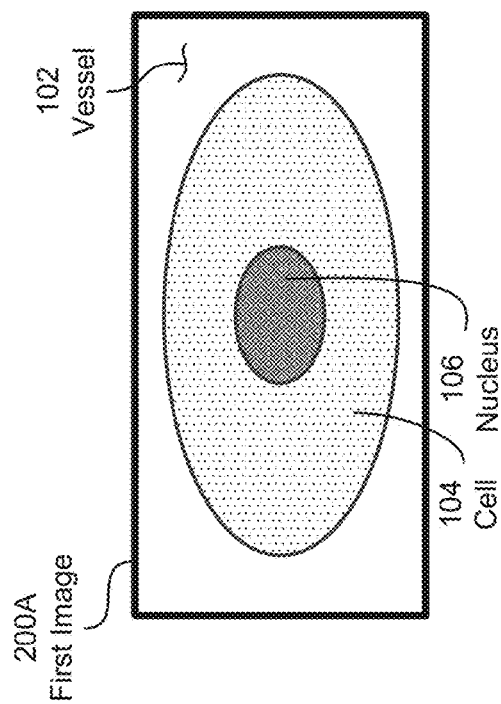
Figure 2C:
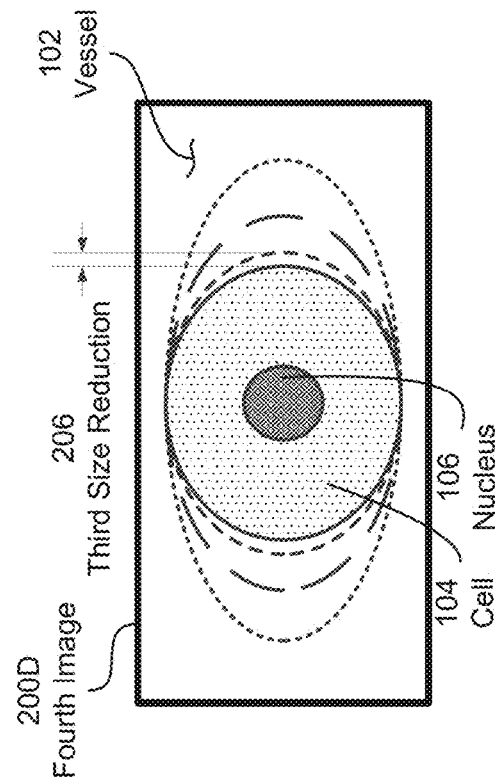
Figure 2D:
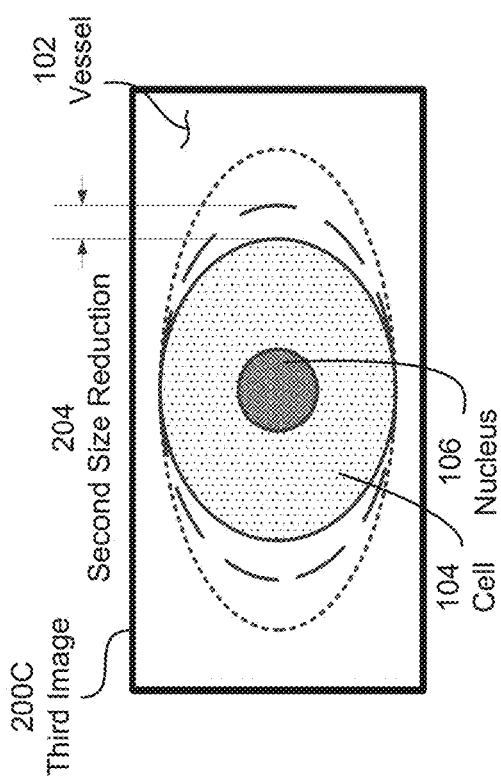

FIGS. 2A-2D are diagrams illustrating the images of cell 104 selected from the image sets obtained at the four different time periods. FIG. 2A shows image 200A obtained, during the first time period, at a focal length corresponding to focal plane 108a. FIG. 2B shows image 200B obtained, during the second time period, at a focal length corresponding to focal plane 108b. FIG. 2C shows image 200C obtained, during the third time period, at a focal length corresponding to focal plane 108c. FIG. 2D shows image 200D obtained, during the fourth time period, at a focal length corresponding to focal plane 108c.

As can be seen from FIGS. 2A-2D, the shape of the cell 104 changes during dissociation. For example, the cell area decreases, as shown via first size reduction 202, second size reduction 204, and third size reduction 206. The rate of change of the cell area may decrease over time during dissociation. As shown in this example, the first size reduction 202 is greater than the second size reduction 204, which in turn is greater than the third size reduction 206.

In some embodiments, a sequence of image sets may be obtained, with each image set including an image of cells in a cell culture vessel obtained for each of multiple different focal lengths, and image features obtained from images in the image sets may be used to determine whether the cells have sufficiently dissociated such that the cell dissociation agent in the cell culture vessel should be neutralized. If it is determined that the cells have not sufficiently dissociated, then the dissociation process may be allowed to continue (e.g., by not neutralizing the cell dissociation agent) and, after additional time passes, a new set of images of the cells may be obtained and image features may be obtained using this new set of images and used to determine whether the cells have sufficiently dissociated. Until it is determined that the cells have sufficiently dissociated, this process may be iterative, with each iteration including: (1) obtaining new images of the cells; (2) extracting image features using the new images (including features obtained only from the new images and difference features obtained based on differences between the new and previously-obtained images); and (3) using the extracted image features to determine whether the cells have sufficiently dissociated while dissociation is ongoing, with periodic imaging of the cells and images of the cells may be obtained.

Figure 4:
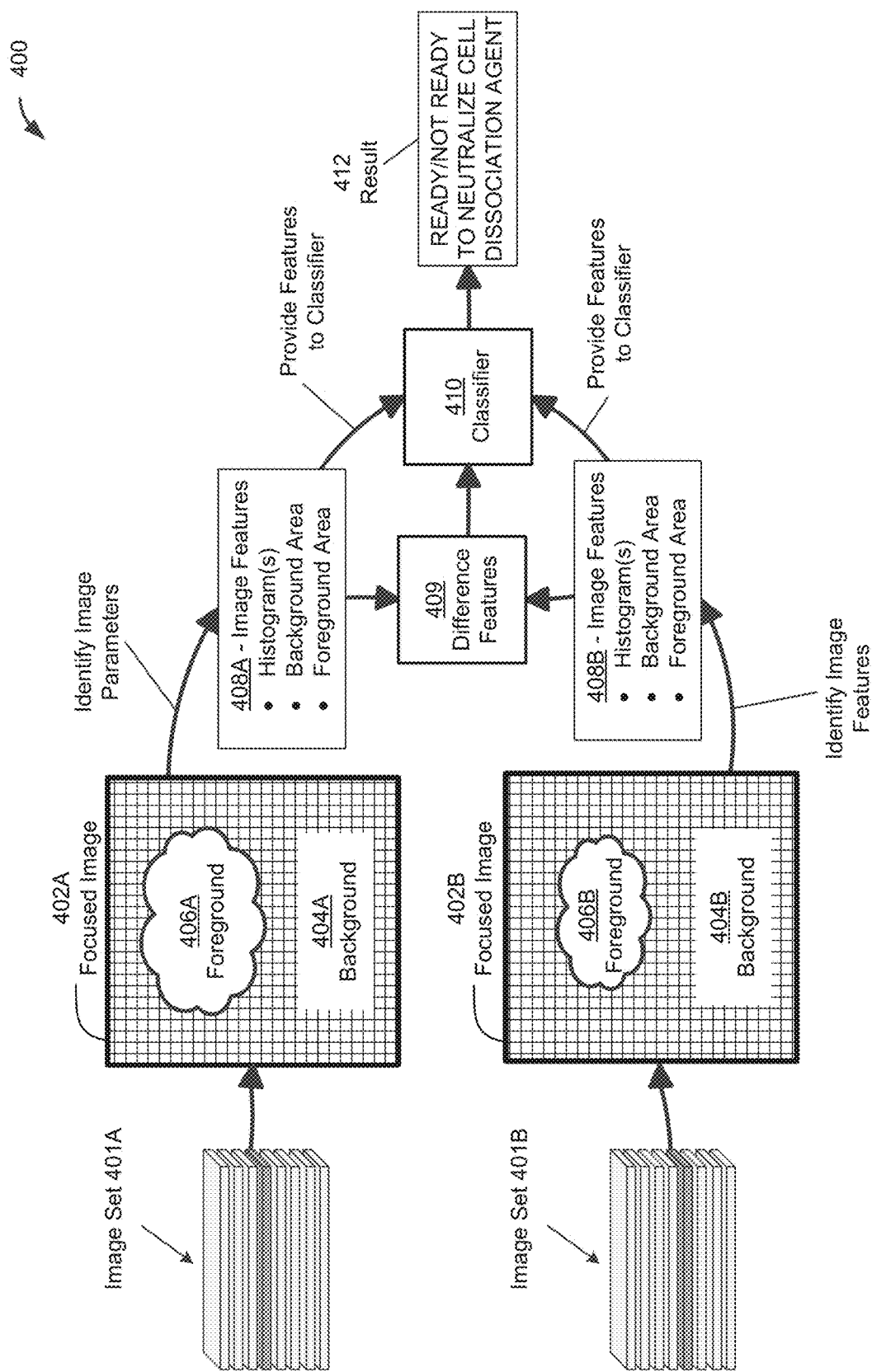
FIG. 4 is a diagram showing an illustrative process for analyzing images of cells to identify when to neutralize the cell dissociation agent, according to some embodiments of the technology described herein.

FIG. 4 illustrates an example iteration of an example iterative process 400 for analyzing images of cells to identify when to neutralize the cell dissociation agent, according to some embodiments of the technology described herein. In the example iteration, two image sets 401A and 401B are obtained, during a first time period and a second time period, respectively. In some embodiments, the images in image sets 401A and 401B may be phase contrast images. The image sets may be obtained using any suitable imaging device such as, for example, the imaging device 604 described with reference to FIG. 6 below.

In some embodiments, the second time period may be a time period that follows the first time period. For example, the image set 401A may consist of images (of cells in a cell culture vessel) obtained at approximately 1 minute after the cell dissociation agent was added to the cell culture vessel and the image set 401B may consist of images obtained approximately 2 minutes after the cell dissociation agent was added to the cell culture vessel. It should be appreciated that the first and second time periods may be time separated by any suitable amount of time (e.g., 5 seconds, 10 seconds, 30 seconds, 1 minute, 1.5 minutes, 2 minutes, 3 minutes, etc.), as aspects of the technology described herein are not limited in this respect.

In some embodiments, the images in image set 401A may include, for each of multiple focal lengths, an image of cells in a cell culture vessel. The images in image set 401B may also include, for each of multiple focal lengths, an image of cells in the cell culture vessel. In some embodiments, the image sets 401A and 401B may consist of the same number of images. For example, each image set may contain an image taken for each of the same set of focal lengths. As another example, each image set may contain images taken for the same number of focal lengths even if one or more of the focal lengths used to obtain image(s) in image set 401A is not used to obtain image(s) in image set 401B. In other embodiments, the image sets 401A and 401B may consist of a different number of images.

Next, a single "focused" image is selected from image sets 401A and 401B to obtain images 402A and 402B, respectively. A focused image may be selected from an image set using edge detection techniques, including the edge detection techniques described with reference to FIG. 5, or in any other suitable way.

Next, each of the images 402A and 402B may be segmented into two portions—a foreground portion and a background portion, with the goal of the foreground portion including the parts of the image that contain cells and the background portion include the parts of the image that do not contain cells. In this illustrative example, image 402A is segmented into background portion 404A and foreground portion 406A. Image 402B is segmented into background portion 404B and foreground portion 406B.

In some embodiments, the result of the segmentation may be represented by a mask such as, for example, a binary mask that indicates for each pixel in an image whether that pixel belongs in the foreground portion or the background portion.

An image may be segmented into foreground and background portions in any suitable way including, for example, edge detection technique(s). As one example, in some embodiments, the segmentation may be performed by: (1) generating a histogram of pixel values in the image; (2) identifying a cut-off threshold using the histogram (e.g., as a point at the bottom of a valley of a histogram); (3) using the cut-off threshold to perform an edge detection algorithm (e.g., the Canny edge detection algorithm); (4) applying erosion and/or dilation operation operators to filter out noise; and (5) fill in holes to get a complete binary mask. In some embodiments, one or more of these steps may be omitted. For example, in some embodiments, segmentation may be performed only using the first two steps. It should be appreciated, however, that segmentation need not be performed using edge detection techniques and may be performed in any other suitable way, as aspects of the technology described herein are not limited in this respect.

After the images 402A and 402B are segmented, image features 408A may be obtained from the image 402A and image features 408B may be obtained from image 402B. Any suitable image features may be extracted from the images. For example, in some embodiments, one or more image features from the following non-limiting list of features may be extracted: (1) area of the background portion in an image (e.g., the area of background portion 404A); (2) area of the foreground portion in the image (e.g., the area of foreground portion 406A); (3) a histogram of pixel intensity values; (4) a histogram of background portion pixel intensity values; (5) a histogram of foreground portion pixel intensity values; (6) light intensity features relating to, for example, characteristics of the intensity values of pixels that comprise an object (e.g., a cell) in the image; and (7) texture features relating to, for example, an appearance of a surface and/or a cross-section of an object (e.g., a cell) in the image. One or more other image features may be obtained in addition to or instead of the above-listed example features.

After image features 408A and 408B are extracted from the images 402A and 402B, respectively, difference features 409 may be computed. A difference feature may indicate how an image feature changed between images. For example, difference features 409 may include a feature indicative of the change between the background area obtained from image 402A and the background area obtained from image 402B. This feature may be obtained by calculating a measure of distance (e.g., difference, absolute difference, and squared difference) between the background areas. As another example, difference features 409 may include a feature indicating the difference between the foreground area obtained from image 402A and the foreground area obtained from image 402B. This feature may also be obtained by calculating a measure of distance (e.g., difference, absolute difference, and squared difference) between the background areas.

As yet another example, difference features 409 may include a feature indicating a measure of distance between the intensity histograms obtained from images 402A and 402B, respectively. For example, difference features 409 may include a feature indicating a measure of distance between foreground intensity histograms, background intensity histograms, or entire image intensity histograms. A measure of distance between two histograms $H_1$ and $H_2$ may be computed in any suitable way. For example, a measure of distance may be obtained using the chi-square distance according to:

$$d(H_1, H_2) = \sum_I \frac{(H_1(I) - H_2(I))^2}{H_1(I)}$$

As another example, a measure of distance may be obtained using a correlation measure according to:

$$d(H_1, H_2) = \frac{\sum_I (H_1(I) - \overline{H}_1)(H_2(I) - \overline{H}_2)}{\sqrt{\sum_I (H_1(I) - \overline{H}_1)^2 \sum_I (H_2(I) - \overline{H}_2)^2}}$$

As yet another example, a measure of distance may be obtained using the intersection measure according to:

$$d(H_1, H_2) = \sum_I \min(H_1(I), H_2(I))$$

As yet another example, a measure of distance may be obtained using Bhattacharyya distance according to:

$$d(H_1, H_2) = \sqrt{1 - \frac{1}{\sqrt{\overline{H}_1 \overline{H}_2 N^2}} \sum_I \sqrt{H_1(I) \cdot H_2(I)}}$$

The above-described illustrative image features may be indicative of changes of cell shape and the rate of such changes. In turn, such changes and their rate may be indicative of the extent to which cells have dissociated from the cell culture vessel being imaged. Accordingly, these image features are then provided as inputs to a classifier 410, the output of which may provide an indication 412 as to whether the cell dissociation agent in the cell culture vessel is to be neutralized and/or whether the cells should be mechanically removed (e.g., via scraping) from the cell culture vessel.

Any suitable classifier may be used as part of this process. For example, a decision tree classifier may be used. As another example, a linear classifier (e.g., Fischer's linear discriminant classifier, logistic regression classifier, Naïve Bayes classifier, probit regression classifier, etc.) may be used. As yet another example, a Bayesian classifier (e.g., a Bayesian network or other graphical model based classifier) may be used. As yet another example, a neural network classifier (e.g., a single layer neural network, a multiplayer neural network, a deep neural network, a recurrent neural network, a convolutional neural network, etc.) may be used. The classifier may be trained with training data that includes image features and corresponding outputs determined manually by one or more cell culture technicians.

The classifier 410 may output a result 412 computed by the classifier based on the image features provides to the classifier as input. In some instances, the result 412 may indicate that it is not yet time to stop the cell dissociation process. In such instances, one or more additional iterations of process 400 may be performed. In other instances, the result 412 may indicate that it is time to stop the cell dissociation process. In such instances, the result 412 may include information indicating whether cells have sufficiently dissociated from the cell culture vessel, information indicating whether cells are to be mechanically removed from the cell culture vessel, information indicating that the cell dissociation agent should be neutralized, and/or any other information indicating that the cells have sufficiently dissociated from the cell culture vessel. The results produced by classifier 410 may be in any suitable format, as aspects of the technology described herein are not limited in this respect.

Figure 5:
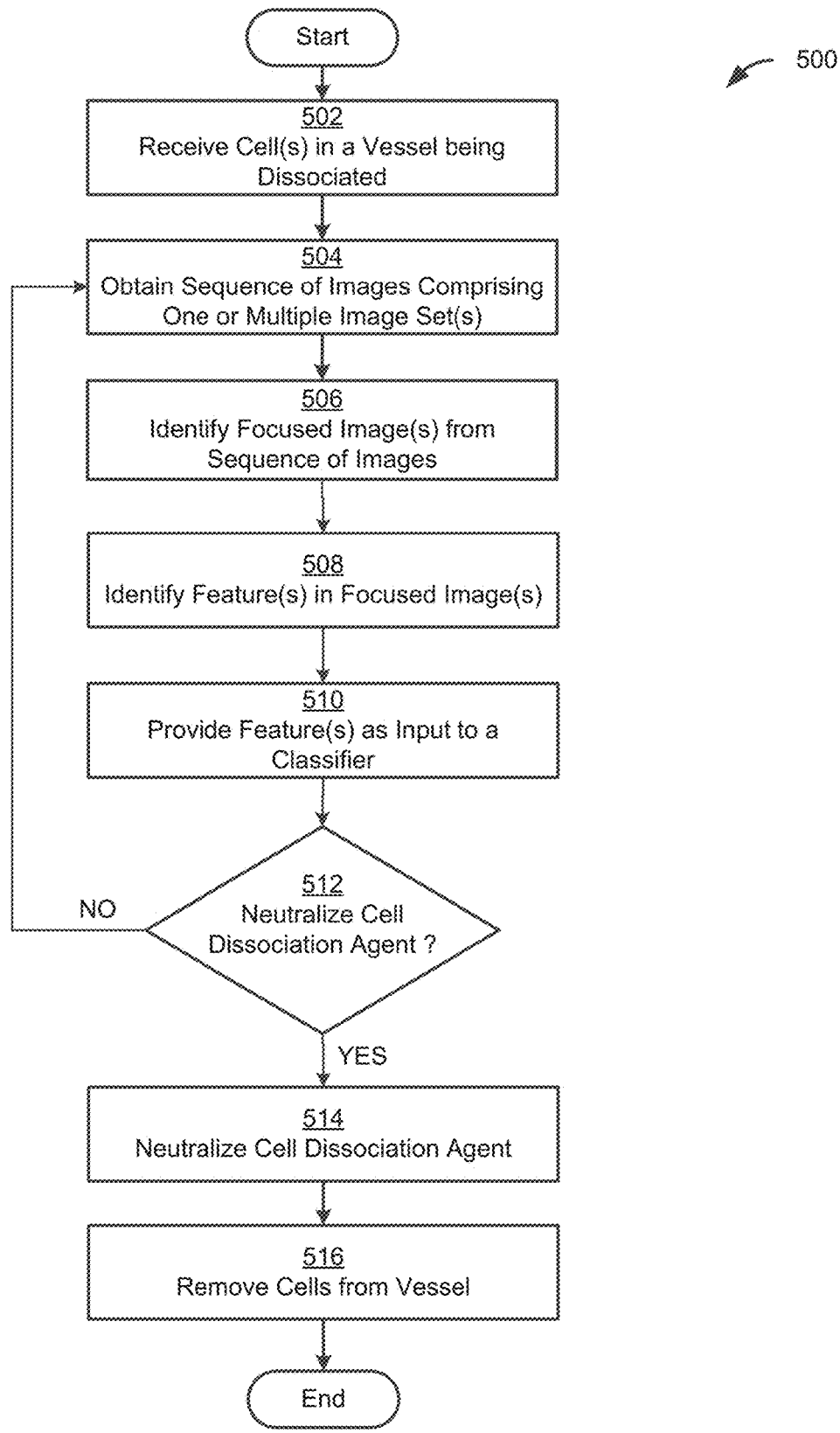
FIG. 5 is a flowchart of an illustrative process for dissociating cells from a vessel, according to some embodiments of the technology described herein.

FIG. 5 is a flowchart of an illustrative process 500 for dissociating cells from a vessel, in accordance with some embodiments of the technology described herein. Process 500 may be performed by any suitable device and, for example, may be performed at least in part by a controller such as, for example, controller 612 described with reference to FIG. 6.

Process 500 begins at act 502, where cells in a cell culture vessel are received in a position where at least some of the cells in the cell culture vessel may be imaged. For example, in some embodiments, the cell culture vessel may be automatically positioned at a location where at least some of the cells may be imaged by an imaging device. For instance, at act 502, a cell culture vessel may be positioned at imaging location 605 within cell culture incubator 600 so that at least some (e.g., all) of the cells in the cell culture vessel may be imaged by imaging device 604.

Next process 500 proceeds to act 504, where a sequence of images is obtained. The images may be obtained using any suitable imaging device(s) and, for example, may be obtained using imaging device 604, which may be a phase-contrast microscope, in some embodiments. Accordingly, in some embodiments, the images obtained at act 504 may be phase contrast images. However, aspects of the technology described herein are not limited to use of only phase contrast images. For example, in other embodiments, one or more of the images obtained at act 504 may be bright field images and/or any other suitable type of images from which information about the degree of cell dissociation may be derived.

In some embodiments, the sequence of images may comprise one or multiple image sets, each of the image sets comprising multiple images of at least some of the cells in the cell culture chamber captured at different focal lengths. In some embodiments, when act 504 is performed for the first time, multiple (e.g., 2, 3, 4, etc.) image sets may be obtained during this first iteration so that image features may be obtained from each of the multiple image sets and differences among these image features (from image set to image set) may be used to determine whether to stop the cell dissociation process. However, in subsequent iterations (resulting from following the "NO" branch of decision block 512), one or multiple image sets may be obtained at act 504. Even if one new image set is obtained during a subsequent iteration, differences between features computed using the new image set and previously-obtained image features may be determined and subsequently used for determining whether to stop the cell dissociation process.

In some embodiments, each image set obtained at act 504 may comprise any suitable number of images. For example, each image set obtained at act 504 may include an image obtained for each of any suitable number of multiple different focal planes (or, equivalently, focal lengths). For example, each image set obtained at act 504 may include an image for each of at least two focal planes, at least five focal planes, at least ten focal planes, at least 50 focal planes, at least 100 focal planes, between 2 and 500 focal planes, or any other suitable range within such ranges. The focal planes may be spaced evenly (e.g., the focal planes are separated by two microns) or unevenly (e.g., some focal planes are separated by one micron and others are separated by three microns). The focal planes used may be selected based on cell type (e.g., thicker cells may warrant using a different set of focal planes than thinner cells).

In some embodiments, when multiple image sets are obtained at act 504, the image sets may be obtained in a one-at-a-time fashion, with at least a threshold amount of time (e.g., at least seconds, at least 20 seconds, at least 30 seconds, at least 1 minute, at least 2 minutes, between 10 seconds and 5 minutes) passing after the first image set is obtained and before beginning to obtain the next image set.

Next, after the sequence of images including one or multiple image sets is obtained at act 504, process 500 proceeds to act 506, where a single image is selected from each of the one or more image sets obtained at act 504 to obtain one or multiple selected images, which will be used for subsequent analysis. The selected images may be termed as "focused" images because, in some embodiments, a selected image may be identified from an image set based on a quantitative estimate of how "focused" the image may be.

In some embodiments, an image may be selected from an image set as a "focused" image by using one or more edge detection techniques. For example, in some embodiments, a focused image may be selected from an image set by detecting cell edges in each image (e.g., using at least one gradient operator, a Sobel edge detector, a Canny edge detector, etc.), determining edge strength (e.g., as a difference in image intensity along the edge), and using the edge strength to compute a focus score (e.g., as a normalized sum of squared edge strengths). The image associated with the smallest focus score may be selected as the focused image in the image set.

In some embodiments, the contrast of the image may be employed to determine the focus score. For example, the contrast of the image may be employed to determine the edge strength. Alternatively (or additionally), the contrast of the image may be employed in combination with (or in place of) the edge strength to generate the focus score.

In some embodiments, an image may be selected from an image set as a "focused" image by: (1) transforming each image in the image set by replacing pixels having an intensity above a brightness threshold with background pixel values; (2) performing edge detection on the transformed images (e.g., by applying the Sobel operator to estimate horizontal and/or vertical changes in gradient intensity); (3) quantifying intensity differences along the edges (which may be considered as an "edge strength") in the images; and (4) using the intensity differences in each transformed image to obtain a "focus" score for the transformed image (e.g., as a normalized sum of squared difference in edge intensities).

In some embodiments, the background pixel values maybe identified using an iterative thresholding technique, sometimes referred to as the "Isodata" algorithm. The technique involves iteratively selecting a threshold between foreground and background of an image by analyzing a histogram of pixel intensities. In some embodiments, a histogram of the pixel intensities may be obtained and initially segmented into two parts using an initial threshold value $\theta_0$ (e.g., which may be determined as half the maximum dynamic range). The sample mean ($m_{f,0}$) of the gray values associated with the foreground pixels and the sample mean ($m_{b,0}$) of the gray values associated with the background pixels may then be computed. A new threshold value $\theta_0$ may then be computed as the average of these two sample means. The process may be repeated, based upon the new threshold, until the threshold value does not change. Accordingly, the threshold may be updated according to:

$$\theta_k = (m_{f,k-1} + m_{b,k-1})/2 \text{ until } \theta_k = \theta_{k-1}.$$

After a focused image is identified, at act 506, for each of the one or more image sets obtained at act 504, process 500 proceeds to act 508, where image features are obtained from the focused image(s). Any suitable image features may be obtained from the focused images.

In some embodiments, image features may be obtained from individual focused images selected at act 506. In order to obtain at least some of the image features, each of the images selected at act 506 may be segmented into foreground and background portions. This may be done in any suitable way including in any of the ways described herein with reference to FIG. 4. The image features obtained at act 508 may include but are not limited to: (1) area of the background portion in an image; (2) area of the foreground portion in the image; (3) a histogram of pixel intensity values; (4) a histogram of background portion pixel intensity values; and (5) a histogram of foreground portion pixel intensity values. One or more other image features may be obtained in addition to or instead of the above-listed example features.

Additionally, in some embodiments, difference features may be calculated at act 508. For example, when multiple image sets are obtained at act 504 and multiple corresponding focused images are identified at act 506, image features (such as the example features described above) may be calculated for each of the multiple focused images, and differences among these features may also be obtained. Techniques for calculating difference features are described herein including with reference to FIG. 5.

Accordingly, in some embodiments, features from individual images as well as difference features computed from multiple images may be obtained and provided as inputs to a classifier at act 510. The classifier may be of any suitable type, examples of which are provided herein including with reference to classifier 410 in FIG. 4.

Next, process 500 proceeds to decision block 512, where a determination is made as to whether the cell dissociation agent should be neutralized. This determination may be made using the result output by the classifier based on the image features provided to the classifier as input at act 510. When the result output by the classifier indicates that it is not yet time to stop the cell dissociation process, process 500 returns, via the "NO" branch, to act 504, where additional images of the cells in the cell culture vessel may be obtained (either immediately or after a threshold amount of time).

On the other hand, when the result output by the classifier indicates that it is time to stop the cell dissociation process, process 500 proceeds to act 514, where the cell dissociation agent is neutralized (e.g., by adding a neutralizing agent and/or additional culture medium), and subsequently to act 516, where the cells are mechanically removed from the cell culture vessel. Cells may be removed mechanically in any suitable way including by scraping, rocking, tapping, and/or ultrasound.

It should be appreciated that process 500 is illustrative and that there are variations. For example, although in the illustrative embodiment, cells are removed mechanically after the cell dissociation agent is neutralized, in other embodiments, the process of mechanically removing the cells may begin prior to neutralizing the cell dissociation agent. This allows for the removal of the cells from the plate earlier in the enzyme treatment process than would otherwise be possible. As another example, rather than collecting image depth stacks having multiple images, in some embodiments, with the help of tapping and ultrasound, only a single image may be collected in each iteration of act 504 for a single corresponding focal length. This removes the need to identify a "focused" image in a depth stack as part of process 500. Accordingly, in such embodiments, act 506 may be omitted.

Figure 6:
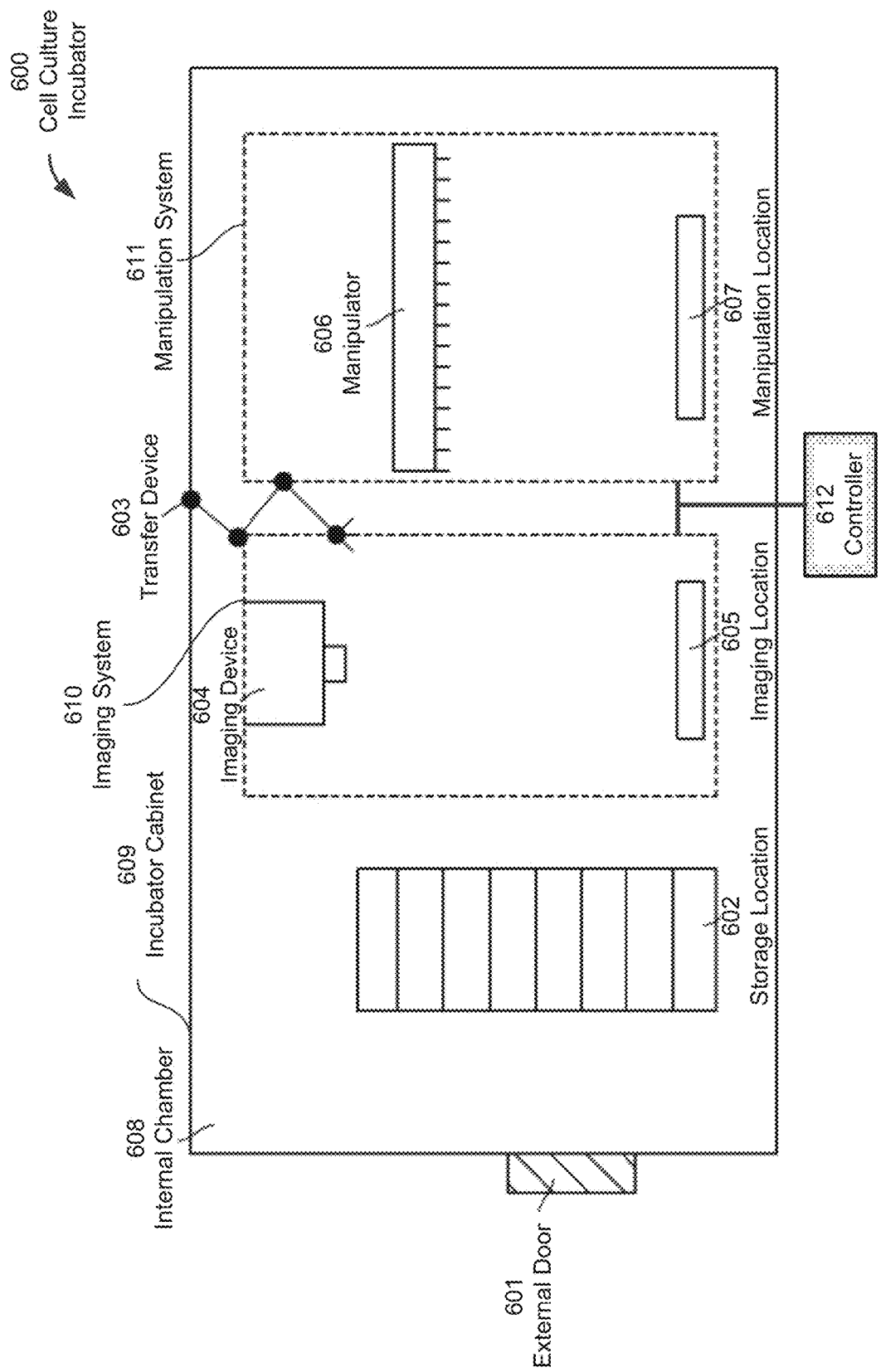
FIG. 6 is a diagram of an illustrative cell culture incubator, according to some embodiments of the technology described herein.

In some embodiments, the techniques described herein may be employed in a cell culture incubator. The cell culture incubator may be constructed to culture cells with little or no manual handling. Thereby, the possibility of the cells becoming contaminated may be reduced or eliminated. An example of such a cell culture incubator is shown in FIG. 6 by cell culture incubator 600. The cell culture incubator 600 includes an incubator cabinet 609 having an internal chamber 608 for incubation of cells in one or more cell culture vessels. The incubator cabinet 609 includes an external door 601 that opens and closes to permit communication between an external environment and the incubator cabinet 609. In some embodiments, the external door 601 opens and closes to permit communication between an external environment and the internal chamber 608. The internal chamber 608 is configured to hold one or more cell culture vessels. The one or more cell culture vessels are stored in a storage location 602. In some embodiments, the storage location 602 is a free-standing structure. For example, a storage location 602 may be a test tube or culture flask rack that can be removed from the internal chamber 608 for loading and unloading of culture vessels. In some embodiments, the storage location 602 is affixed to a surface of the internal chamber 608. For example, the storage location 602 may be a series of racks or shelves that are connected to the walls or floor of the internal chamber 608 and are thus not able to be removed from the incubator cabinet 609.

In some embodiments, the cell culture incubator 600 includes a transfer device 603 for moving one or more cell culture vessels. The transfer device 603 may be affixed to any appropriate surface of the internal chamber 608. For example, the transfer device 603 may be affixed to the top or ceiling of the internal chamber 608. Alternatively, the transfer device 603 may be affixed to a side wall of the internal chamber 608. In some embodiments, the transfer device 603 is not affixed to the wall of the internal chamber 608. For example, the transfer device 603 may rest on a wheeled tripod or other mobile structure that can be moved around the internal chamber 608.

In some embodiments, the transfer device 603 moves one or more cell culture vessels from the storage location 602 to an imaging location 605 in an imaging system 610 or to a manipulation location 607 in a manipulation system 611. The transfer device 603 can also move one or more cell culture vessels from an imaging location 605 to a manipulation location 607 or from a manipulation location 607 to an imaging location 105. When imaging or manipulation are complete, the transfer device 603 moves one or more cell culture vessels from an imaging location 605 or a manipulation location 607 to a storage location 602.

In some embodiments, the transfer device 603 may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, the transfer device 603 may include one or more robotic elements. For example, the transfer device 603 may include a robotic arm capable of gripping, lifting, pushing, grabbing, sliding, rotating, translating, releasing, raising, lowering, and/or tilting one or more cell culture vessels. In some cases, the transfer device 603 selectively and releasably grips one or more cell culture vessels. In certain embodiments, a transfer device 603 may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator cabinet (e.g., within a storage array in an internal chamber).

In some embodiments, the incubator cabinet 609 includes the imaging location 605 and the manipulation location 607. In some embodiments, the imaging location 605 is located on a surface of the internal chamber 608 opposite from an imaging device 604. In some embodiments, the imaging location 605 is a platform, either free-standing or affixed to a surface of the internal chamber 608. In some embodiments, the platform is movable. For example, a movable platform may be affixed to two or more rods that allow the platform to be moved left, right, forward, backward, up or down in relation to the imaging device 604. In some embodiments, the movable platform is motorized.

In some embodiments, the imaging system 610 may be configured to capture images of cells in cell culture vessels when the vessels are at the imaging location 608. For example, the imaging system may be configured to capture phase-contrast images (sometimes termed "phase-shift" images) and/or bright-field images of the cells in the cell culture vessels. A phase-contrast image may be a topographical image of an object and may include information about optical distances. In some embodiments, a phase-contrast image may provide information about transparent objects, such as living biological cells. A bright-field image may be captured by, for example, illuminating a sample and producing an image based on the light absorbed by the sample. The imaging system 610 may comprise an imaging device 604 configured to measure light (e.g., transmitted or scattered light), color, morphology, and/or other detectable parameters. The imaging device 604 may be, for example, a monochrome imaging device, a red-green-blue (RGB) imaging device, a spectral imaging device, a fluorescence imaging device, and/or a multi-channel imaging device. In certain embodiments, the imaging system 610 includes one or more lenses, fibers, apertures, mirrors, light sources (e.g., a laser or lamp), or other optical elements. The imaging system 610 may be implemented as a microscope (e.g., bright-field microscope, a fluorescence microscope, and/or a phase-contrast microscope). For example, the imaging system 610 may be implemented as an optical microscope configured to operate as a bright-field microscope (for generating bright-field images) and/or a phase-contrast microscope (for generating phase-contrast images).

In some embodiments, the manipulator system 611 includes a manipulator 606 that manipulates the cells of cell culture vessels when the vessels are at the manipulation location 607. In some embodiments, the manipulator 606 has an array of needles, capillaries, pipettes, and/or micromanipulators. For example, the manipulator 606 may include a cell picker. In some embodiments, a manipulator 606 comprises one or more cell pickers. In some embodiments, the manipulator 606 may include a cell scraper comprising a scraping edge suitable for scraping cells off of a surface. In some embodiments, the scraping edge is a portion of a cell scraper contactable with the surface of a cell culture vessel or other surface and suitably configured for scraping matter from the surface for cleaning the surface and/or for scraping cells adhering to the surface without substantially killing the cells, e.g., by mechanically lysing the cells. In some embodiments, it is desirable for a scraping edge or scraping edge assembly to be disposable in order to prevent cross-contamination between cell cultures. Thus, in some embodiments, the scraping edge or scraping edge assembly is disposable.

In some embodiments, the cell culture incubator 600 includes a controller 612 that is configured to control operation of one or more components in the cell culture incubator 600 such as the imagining system 610, the manipulator system 611, and/or the transfer device 603. The controller 612 may be configured to perform one or more acts in the methods described above. For example, the controller 612 may provide instructions to the transfer device 603 to cause the transfer device to move a cell culture vessel to the imaging location 605 and provide instructions to the imaging system 610 to capture an image of the cells in the cell culture vessel.

The controller 612 may be implemented in any of a variety of ways. An illustrative implementation of the controller 612 is shown in FIG. 7 by controller 700. As shown, the controller 700 may include one or more computer hardware processors 702 and one or more articles of manufacture that comprise non-transitory computer-readable storage media (e.g., memory 704 and one or more non-volatile storage devices 706). The processor(s) 702 may control writing data to and reading data from the memory 704 and the non-volatile storage device(s) 706 in any suitable manner. To perform any of the functionality described herein, the processor(s) 702 may execute one or more processor-executable instructions stored in one or more non-transitory computer-readable storage media (e.g., the memory 704), which may serve as non-transitory computer-readable storage media storing processor-executable instructions for execution by the processor(s) 702.

It should be appreciated that various alterations may be made to the controller 700 without departing from the scope of the present document. In some embodiments, one or more components of the controller 700 shown in FIG. 7 may be separate from the controller 700 and communicatively coupled to the controller 700. For example, the memory 704 and/or one or more non-volatile storage devices 706 may be separate from the controller 700.

The terms "program" or "software" are used herein in a generic sense to refer to any type of computer code or set of processor-executable instructions that may be employed to program a controller or processor to implement various aspects of embodiments as discussed above. Additionally, according to one aspect, one or more computer programs that when executed perform methods of the disclosure provided herein need not reside on a single controller or processor, but may be distributed in a modular fashion among different controllers or processors to implement various aspects of the disclosure provided herein.

Processor-executable instructions may be in many forms, such as program modules, executed by one or more controllers or other devices. Generally, program modules include routines, programs, objects, components, data structures, etc. that perform particular tasks or implement particular abstract data types. Typically, the functionality of the program modules may be combined or distributed.

Aspects of the disclosure relate to incubators and methods for culturing, manipulating, and/or monitoring cells under controlled conditions (e.g., under aseptic and/or sterile conditions). In some embodiments, cell cultures are grown within a culture vessel in an incubator of the disclosure. As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with an imaging system. In some embodiments, a cell culture vessel includes one or more portions that are substantially non-reflective.

Cell culture vessels may be configured for culturing cells of different types, including eukaryotic or prokaryotic cells. In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis*, or *Pischia pastoris* cells, or bacterial cells such as *Escherichia coli, Bacillus subtilis*, or *Corynebacterium* cells), insect cells (e.g., *Drosophila* cells, or Sf9 or Sf21 cells), plant cells (e.g., algal cells) or cells of any other type.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells) and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, *Xenopus* cell lines, plant cell lines, or any other cell lines. In some embodiments, cells are human 293 cells (e.g., 293-T or HEK 293 cells), murine 3T3 cells, Chinese hamster ovary (CHO) cells, CML TI cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators disclosed herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or pronase are used to digest the extracellular matrix. In some embodiments, tissue or biological samples are placed in culture medium (e.g., with or without physical or enzymatic disruption) and cells that are released and that grow in the culture medium can be isolated for further culture.

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example, for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof. In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNTfamily proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated as part of an incubator provided herein.

In some aspects, the incubators and methods described herein provide and maintain appropriate temperature and gas mixtures for cell growth. It should be appreciated that cell growth conditions differ for different cell types and that the incubators described herein can be programmed to maintain different conditions. In some embodiments, conditions of approximately 37° C., and 5% $CO_2$ are used for mammalian cells.

In some embodiments, devices and methods described herein are used to monitor or assay the culture media for nutrient depletion, changes in pH, changes in temperature accumulation of apoptotic or necrotic cells, and/or cell density. In some embodiments, devices and methods described herein are used to modify or change the culture media or conditions and/or to passage the cell cultures when appropriate. In some embodiments, these procedures are automated.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator coupled to a computer, capable of automatically monitoring and adjusting cell culture conditions for optimal growth of the cell culture.

In some embodiments, cells are passaged within an incubator cabinet described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture within an incubator cabinet of an incubator herein. For example, cell cultures may be transfected with nucleic acids (e.g., DNA or RNA) or exposed to viral infection (e.g., using recombinant virus particles to deliver DNA or RNA), while for example, remaining within an incubator cabinet of an incubator provided herein.

It should be appreciated that aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving) surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by *mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling or other enzymatic techniques) or cell-based assays can be used to detect contamination (e.g., *mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat-STR-fingerprinting), isoenzyme analysis, human lymphocyte antigen (HLA) typing, chromosomal analysis, karyotyping, cell morphology, or other techniques.

In some embodiments, cells produced using the incubators or methods described herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into the wall of the incubator cabinet).

In some embodiments this document relates to incubators and methods for culturing, manipulating, and/or monitoring cells under controlled conditions (e.g., under aseptic and/or sterile conditions). In some embodiments, the cell culture incubators included an incubator cabinet having an internal chamber for incubation of cells in one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, incubators include a storage location within the internal chamber for storing one or more cell culture vessels.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., cameras, barcode readers), electrical elements (e.g., circuits, cables, power cords, and power supplies such as batteries, generators, and direct or alternating current supplies), controllers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

In some embodiments, incubators or incubator cabinets provided herein are rectangularly cuboidal in shape. In some embodiments incubators or incubator cabinets provided herein have a rectangular footprint in a range of 1 $ft^2$ to 16 $ft^2$. In some embodiments incubators or incubator cabinets provided herein have a rectangular footprint of up to about 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, 11 $ft^2$, 12 $ft^2$, 13 $ft^2$, 14 $ft^2$, 15 $ft^2$, or 16 $ft^2$. In some embodiments incubators or incubator cabinets provided herein have a total chamber volume in a range of 1 $ft^3$ to 100 $ft^3$. In some embodiments incubators or incubator cabinets provided herein have a chamber volume of up to about 1 $ft^3$, 5 $ft^3$, 10 $ft^3$, 25 $ft^3$, 50 $ft^3$ or 100 $ft^3$. In some embodiments incubators or incubator cabinets provided herein have a rectangular footprint in a range of 0.09 $m^2$ to 1.78 $m^2$. In some embodiments incubators or incubator cabinets provided herein have a rectangular footprint of up to about 0.1 $m^2$, 0.2 $m^2$, 0.3 $m^2$, 0.4 $m^2$, 0.5 $m^2$, 0.6 $m^2$, 0.7 $m^2$, 0.8 $m^2$, 0.9 $m^2$, 1.0 $m^2$, 1.1 $m^2$, 1.2 $m^2$, 1.3 $m^2$, 1.4 $m^2$, 1.5 $m^2$, 1.6 $m^2$, or 1.7 $m^2$. In some embodiments, incubators or incubator cabinets provided herein have a total chamber volume in a range of 0.03 $m^3$ to 3 $m^3$. In some embodiments incubators or incubator cabinets provided herein have a chamber volume of up to about 0.03 $m^3$, 0.1 $m^3$, 0.3 $m^3$, 1 $m^3$, or 3 $m^3$.

As used herein, a "storage location" refers to a location at which one or more cell culture vessels is stored (e.g. within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that is molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager.

In some embodiments, an incubator cabinet is single-walled. In some embodiments, an incubator is double-walled. In some embodiments, insulation material is provided between the double walls of an incubator cabinet to control heat loss from the incubator cabinet and facilitate temperature control in the incubator cabinet. In some embodiments, the outer wall of an incubator cabinet comprises a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

In some embodiments, the environment inside an incubator is controlled by a control system that may be configured to control the temperature, humidity, carbon dioxide, oxygen and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, N2, $CO_2$, $O_2$ and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents. In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator).

In some embodiments, an incubator can include one or more light sources (e.g., an incandescent bulb, LED, UV or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator provided herein.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a controller. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

In some embodiments, an incubator (e.g., an internal chamber, and/or a transfer chamber of an incubator cabinet) comprises one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoroethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactant with carbon dioxide or ozone.

As used herein, a "transfer device for moving one or more items" refers to a device that can transfer one or more items from a first location to a second location. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In certain embodiments, the transfer device may transfer one or more items to or from multiple locations in an incubator. For example, a transfer device may be used to move a pipette to a maintenance location in an internal chamber for maintenance of one or more cell culture vessels. In some embodiments, an incubator includes more than one transfer device for moving one or more items (e.g., two or more separate transfer devices for transferring items between and within chambers).

A transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a transfer device may include one or more robotic elements. For example, a transfer device may include a robotic arm capable of gripping, lifting, pushing, grabbing, sliding, rotating, translating, releasing, raising, lowering, and/or tilting one or more items (e.g., pipettes). In preferred embodiments, the transfer device selectively and releasably grips one or more pipettes. In certain embodiments, a transfer device may include an arm coupled to a mechanical gripper. For example, an arm may include a mechanical gripper at or near one end for releasably gripping a pipette and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more items (e.g., pipettes) at different horizontal and vertical positions within an incubator (e.g., within a storage array in an internal chamber).

As used herein, a "cell culture vessel transfer device" refers to a device that can transfer one or more cell culture vessels from a first location to a second location. In certain embodiments, the transfer device may transfer one or more items to or from multiple locations in an incubator. For example, a cell culture vessel transfer device may be used to move a cell culture vessel from a transfer chamber to an internal chamber, and/or from a storage location to an imaging location. In some embodiments, an incubator includes more than one transfer device for moving one or more items (e.g., separate means for transferring items between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In preferred embodiments, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator (e.g., within a storage array in an internal chamber).

In some embodiments, a transfer device includes a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further can include a gripper assembly coupled to a robotic arm. In some embodiments, the gripper assembly includes one or more grippers mounted on the end or near the end of the robotic arm, each gripper including two or more (e.g., 3, 4, 5, or more) gripper fingers. In some embodiments, each of the gripper fingers of the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, the platform, or a separate absolute encoder for each of the gripper assembly the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt located, for example on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components between a transport line of the laboratory automation system and the incubator cabinet or the external assay components and the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are located. In some case, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to properly position the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner. In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc. In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container, or the system itself may determine measure the height of the vessel or other container. Using this information, the robotic arm may be requested to transport a particular container, such as when an analytical module is ready to perform an assay or other manipulation on cells grown in the vessels or has completed performing an assay or manipulation.

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

In some embodiments, a component (e.g., a controller) controls various processes performed inside the incubator. For example, a controller may direct control equipment (e.g., a manipulator, an imager, a fluid handling system, etc.). In some embodiments, the controller controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

In some embodiments, incubators provided herein are configured to permit digital identification and marking of cells. For example, a cell or cells may be cultured in an incubator described herein and imaged via fluorescent microscopy to digitally mark (e.g., via a computer having imaging software that is coupled to the incubator) a cell or cells (e.g., a cell population) of interest (e.g., cells positive for fluorescence). The location of the marked cells can be stored on the computer's memory and accessed at a later time point. The digital marking of cell populations may permit marked cells to be subsequently viewed or manipulated. The subsequent viewing, and/or manipulating may be performed at the same location (e.g., an imaging location) at which the cells were digitally marked, or at a location remote from the location at which the cells were digitally marked (e.g., a manipulation location that is not the imaging location). In some cases, the digital marking of a cell or cells may be facilitated by alignment of the cell culture vessel housing said cells to the imager via one or more fiducial marks. In some embodiments, an incubator as described herein comprises a plurality of workstations (e.g., 1, or 2, or 3, or 4, or 5, or more workstations), wherein each workstation is configured to permit digital identification and marking of cells.

In certain embodiments, incubators provided herein are configured to permit high-throughput screening (HTS) within an incubator cabinet. In some embodiments, HTS refers to testing of up to, and including, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays disclosed herein involve the use of automation. In some embodiments, an integrated robot system that includes one or more robotic arms transports assay microplates between multiple assay stations for compound, cell and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

Various inventive concepts may be embodied as one or more processes, of which examples have been provided including, for instance, the process described with reference to FIG. 5. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term). The phraseology and terminology used herein is for the purpose of description and should not be regarded as limiting. The use of "including," "comprising," "having," "containing," "involving," and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A cell culture incubator comprising: an incubator cabinet configured to receive a cell culture vessel storing a plurality of cells being dissociated from at least one surface of the cell culture vessel by at least one cell dissociation agent; an imaging system configured to image the plurality of cells; and at least one controller coupled to the imaging system; the at least one controller coupled to memory containing instructions that when executed: control the imaging system to capture a sequence of images of at least some cells in the plurality of cells during dissociation; and use the sequence of images to identify when to neutralize the at least one cell dissociation agent, wherein capturing the sequence of images comprises capturing a first plurality of images of the at least some cells in a plurality of focal planes and subsequently capturing a second plurality of images of the at least some cells in a plurality of focal planes.

2. The cell culture incubator of claim 1, wherein identifying when to neutralize the at least one cell dissociation agent is based, at least in part, on a measure of distance between a first image in the first plurality of images and a second image in the second plurality of images.

3. The cell culture incubator of claim 2, wherein the identifying when to neutralize the at least one cell dissociation agent includes calculating a measure of the distance between the first image and the second image.

4. The cell culture incubator of claim 3, wherein calculating a measure of the distance between the first image and the second image, at least in part, comprises calculating a measure of distance between a first intensity histogram of the first image and a second intensity histogram of the second image.

5. A cell culture incubator comprising: an incubator cabinet configured to receive a cell culture vessel storing a plurality of cells being dissociated from at least one surface of the cell culture vessel by at least one cell dissociation agent; an imaging system configured to image the plurality of cells; and at least one controller coupled to the imaging system; the at least one controller coupled to memory containing instructions that when executed: control the imaging system to capture a sequence of images of at least some cells in the plurality of cells during dissociation; and use the sequence of images to identify when to neutralize the at least one cell dissociation agent, wherein identifying when to neutralize the at least one cell dissociation agent using the sequence of images at least in part comprises:
obtaining at least one feature using at least one image in the sequence of images;
providing the at least one feature as input to a classifier; and
determining when to neutralize the at least one dissociation agent based on the output of said classifier generated using the at least one feature as an input.

6. The cell culture incubator of claim 5, wherein obtaining the at least one feature using the at least one image at least in part comprises calculating a measure of distance between a first intensity histogram of a first image in the sequence of images and a second intensity histogram of a second image in the sequence of images.

7. The cell culture incubator of claim 6, wherein the at least one controller is configured to provide the at least one feature as input to the classifier at least in part by providing the measure of distance between the first intensity histogram and the second intensity histogram as input to the classifier.

8. The cell culture incubator of claim 5, wherein the classifier is selected from the group consisting of: a decision tree, a neural network, a discriminant function, a Bayesian network, and a support vector machine.

9. A method performed in a cell culture incubator comprising the steps of: receiving a cell culture vessel storing a plurality of cells being dissociated from at least one surface of the cell culture vessel by at least one cell dissociation agent; imaging the plurality of cells by capturing a sequence of images of at least some cells in the plurality of cells during dissociation; and using the sequence of images to identify when to neutralize the at least one cell dissociation agent, wherein determining when to neutralize the at least one cell dissociation agent comprises obtaining at least one feature using at least one image in the sequence of images, providing the at least one feature as input to a classifier and determining based on output of the classifier generated using the at least one feature as input.

10. The method of claim 9, wherein obtaining the at least one feature using the at least one image at least in part comprises calculating a measure of distance between a first intensity histogram of a first image in the sequence of images and a second intensity histogram of a second image in the sequence of images.

11. The method of claim 10, wherein providing the at least one feature as input to the classifier at least in part comprises providing the measure of distance between the first intensity histogram and the second intensity histogram as input to the classifier.

12. The method of claim 9, wherein the classifier is selected from the group consisting of: a decision tree, a neural network, a discriminant function, a Bayesian network, and a support vector machine.

13. A method performed in a cell culture incubator comprising the steps of: receiving a cell culture vessel storing a plurality of cells being dissociated from at least one surface of the cell culture vessel by at least one cell dissociation agent; imaging the plurality of cells by capturing a sequence of images of at least some cells in the plurality of cells during dissociation; and using the sequence of images to identify when to neutralize the at least one cell dissociation agent, wherein capturing includes obtaining a sequence of image sets, each image set containing, for each of a plurality of focal planes, an image of the at least some cells in the plurality of cells.

14. The method of claim 13, wherein identifying when to neutralize the at least one dissociation agent using the sequence of images, at least in part, comprises:
 selecting a first focused image based on a focus score calculated based, at least in part, on an edge strength of at least one cell in the plurality of cells;
 selecting a second focused image based on a focus score calculated based, at least in part, on an edge strength of at least one cell in the plurality of cells;
obtaining at least one feature using first said focused image and said second focused image;
 providing the at least one feature as input to a classifier; and
 determining when to neutralize the at least one cell dissociation agent based, at least in part, on an output of the classifier generated using the at least one feature as input.

15. The method of claim 14, wherein obtaining the at least one feature includes calculating a measure of distance between a first intensity histogram of the first focused image and a second intensity histogram of the second focused image.

16. The method of claim 14, wherein the edge strength of the at least one cell is determined using at least one gradient operator.

17. The method of claim 14, wherein the edge strength of the at least one cell is determined using a Sobel edge detector or a Canny edge detector.

18. A method performed in a cell culture incubator, comprising the steps of:
 receiving in a cell culture incubator a cell culture vessel storing a plurality of cells being dissociated from at least one surface of the cell culture vessel by at least one cell dissociation agent;
 capturing, by an imaging system in the cell culture incubator, a sequence of images of at least some cells in the plurality of cells during dissociation; and
 identifying, using at least one controller coupled to the imaging system, when to neutralize the at least one cell dissociation agent using the sequence of images;
 wherein capturing the sequence of images comprises capturing a first plurality of images of the at least some cells in a plurality of focal planes and subsequently capturing a second plurality of images of the at least some cells in a plurality of focal planes.

19. The method of claim 18, wherein identifying when to neutralize the at least one cell dissociation agent comprises identifying when to neutralize the at least one cell dissociation agent based, at least in part, on a measure of distance between a first image from the first plurality of images and a second image from the second plurality of images.

20. The method of claim 18, further comprising calculating the measure of the distance between the first image and the second image.

21. A method performed in a cell culture incubator, comprising the steps of:
 receiving in a cell culture incubator a cell culture vessel storing a plurality of cells being dissociated from at least one surface of the cell culture vessel by at least one cell dissociation agent;
 capturing, by an imaging system in the cell culture incubator, a sequence of images of at least some cells in the plurality of cells during dissociation;
 identifying, using at least one controller coupled to the imaging system, when to neutralize the at least one cell dissociation agent using the sequence of images; and
 adding at least one cell culture medium to the cell culture vessel in response to identifying when to neutralize the at least one cell dissociation agent.

* * * * *